(12) United States Patent
Rajan

(10) Patent No.: US 9,259,163 B2
(45) Date of Patent: Feb. 16, 2016

(54) INTEGRATED WIRELESS NON-INVASIVE PERFUSION SENSOR AND METHOD OF USE

(75) Inventor: Vinayakrishnan Rajan, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 718 days.

(21) Appl. No.: 13/115,231

(22) Filed: May 25, 2011

(65) Prior Publication Data

US 2012/0302889 A1    Nov. 29, 2012

(51) Int. Cl.
| | | |
|---|---|---|
| *A61B 5/02* | (2006.01) | |
| *A61B 5/026* | (2006.01) | |
| *A61B 5/00* | (2006.01) | |
| *A61N 1/365* | (2006.01) | |
| *A61N 1/39* | (2006.01) | |

(52) U.S. Cl.
CPC ............ *A61B 5/0261* (2013.01); *A61B 5/6823* (2013.01); *A61B 5/6824* (2013.01); *A61B 5/6826* (2013.01); *A61B 5/6828* (2013.01); *A61B 5/6831* (2013.01); *A61B 5/6833* (2013.01); *A61B 2560/0412* (2013.01); *A61N 1/36514* (2013.01); *A61N 1/3956* (2013.01)

(58) Field of Classification Search
CPC ..................... A61B 2560/0412; A61B 5/0261; A61B 5/6823; A61B 5/6824; A61B 5/6826; A61B 5/6828; A61B 5/6831; A61B 5/6833; A61N 1/36514; A61N 1/3956
See application file for complete search history.

(56) References Cited

U.S. PATENT DOCUMENTS

| | | | | |
|---|---|---|---|---|
| 3,915,572 A | * | 10/1975 | Orloff | ........................ 356/28.5 |
| 5,601,611 A | | 2/1997 | Fayram | |
| 5,865,749 A | | 2/1999 | Doten | |
| 6,178,342 B1 | | 1/2001 | Borgos et al. | |
| 6,259,947 B1 | | 7/2001 | Olson | |
| 7,013,178 B2 | | 3/2006 | Reinke | |
| 7,092,759 B2 | | 8/2006 | Nehls | |
| 7,097,618 B1 | | 8/2006 | Benditt | |
| 7,139,613 B2 | | 11/2006 | Reinke | |
| 7,529,583 B1 | | 5/2009 | Brockway | |
| 7,580,752 B2 | | 8/2009 | Gerber | |
| 7,684,864 B2 | | 3/2010 | Olson | |
| 7,708,695 B2 | | 5/2010 | Akkermans | |
| 7,769,451 B2 | | 8/2010 | Yang | |
| 7,819,812 B2 | * | 10/2010 | John et al. | ..................... 600/504 |
| 7,894,894 B2 | | 2/2011 | Stadler | |

(Continued)

OTHER PUBLICATIONS

P0040105WOU1 (PCT/US2012/036433) PCT Notification of Transmittal of the International Search Report and the Written Opinion of the International Searching Authority, Mailed Aug. 10, 2012, 15 pages.

(Continued)

*Primary Examiner* — Ruth S Smith
(74) *Attorney, Agent, or Firm* — Evans M. Mburu

(57) ABSTRACT

A system and associated method provide tissue perfusion monitoring in a patient. A laser Doppler unit is provided including a coherent laser light source and a photodetector. A processor is configured to receive a signal from the photodetector and determine a tissue perfusion measurement from a Doppler-shifted component of the photodetector signal. A wireless communication circuit transmits the tissue perfusion measurement. A power source provides power to the laser Doppler unit, the processor and the communication circuit. A wireless housing encloses the laser Doppler unit, the processor, the power source and the communication circuit.

19 Claims, 7 Drawing Sheets

(56) References Cited

U.S. PATENT DOCUMENTS

| | | | |
|---|---|---|---|
| 2006/0253160 A1 | 11/2006 | Benditt et al. | |
| 2007/0129769 A1 | 6/2007 | Bourget | |
| 2008/0081963 A1 | 4/2008 | Naghavi | |
| 2008/0234590 A1* | 9/2008 | Akkermans et al. | 600/504 |
| 2009/0118651 A1* | 5/2009 | Rousso et al. | 601/134 |
| 2009/0143655 A1* | 6/2009 | Shani | 600/323 |
| 2009/0163968 A1 | 6/2009 | Donofrio | |
| 2009/0209871 A1 | 8/2009 | Ueki | |
| 2009/0269716 A1* | 10/2009 | Jenkins et al. | 433/72 |
| 2009/0326350 A1* | 12/2009 | Kracker | 600/324 |
| 2010/0022990 A1* | 1/2010 | Karpowicz et al. | 604/543 |
| 2010/0105997 A1 | 4/2010 | Ecker et al. | |
| 2010/0182415 A1* | 7/2010 | Elster et al. | 348/77 |
| 2010/0268056 A1* | 10/2010 | Picard et al. | 600/388 |

OTHER PUBLICATIONS

Moor Instruments: "Tissue Blood Flow and Temperature Monitoring with moorVMS-LDF", Located from the internet at URL: http://gb.moor.co.uk/product/moorvms-1df-laser-doppler-monitor/1/o/4/brochure, Sep. 23, 2008, 4 pages.

Clough, et al., "Evaluation of a New High Power, Wide Separation Laser Doppler Probe: Potential Measurement of Deeper Tissue Blood Flow", Microvascular Research, Academic Press, vol. 78, No. 2, Sep. 1, 2009, pp. 155-161.

Moor Instruments: "Tissue Blood Flow and Temperature Monitoring with DRT4", Located from the internet at URL: http//us.moor.co.uk/productx/drt4-drt4/11/o/4/brochure, Feb. 6, 2008, 6 pages.

R. F. Bonner and R. Nossal "Model for laser Doppler measurements of blood flow in tissue," Appl. Opt., 1981 2097-2107, vol. 20.

* cited by examiner

INTEGRATED WIRELESS NON-INVASIVE PERFUSION SENSOR AND METHOD OF USE

TECHNICAL FIELD

The disclosure relates generally to medical devices and, in particular, to an apparatus and method for monitoring tissue perfusion using laser Doppler flowmetry (LDF).

BACKGROUND

Implantable physiological sensors are used for monitoring patient conditions and for managing or controlling therapies delivered to a patient. For example, there are numerous reasons that a clinician is interested in monitoring the hemodynamic status of a patient. Various implantable sensors such as blood pressure sensors, oxygen sensors, impedance sensors, acoustical sensors or the like have been proposed or used to monitor physiological signals in the body to obtain surrogate measures for cardiac output or other clinical hemodynamic parameters. Reliable, ambulatory monitoring of a hemodynamic parameter can be useful in controlling numerous types of device delivered therapies, such as cardiac resynchronization therapy (CRT) used to treat heart failure or cardioversion defibrillation shocks used to treat hemodynamically unstable arrhythmias. A need remains for miniaturized physiological sensors that have low power requirements and provide reliable sensing of signals that can be used to monitor the hemodynamic status of a patient.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
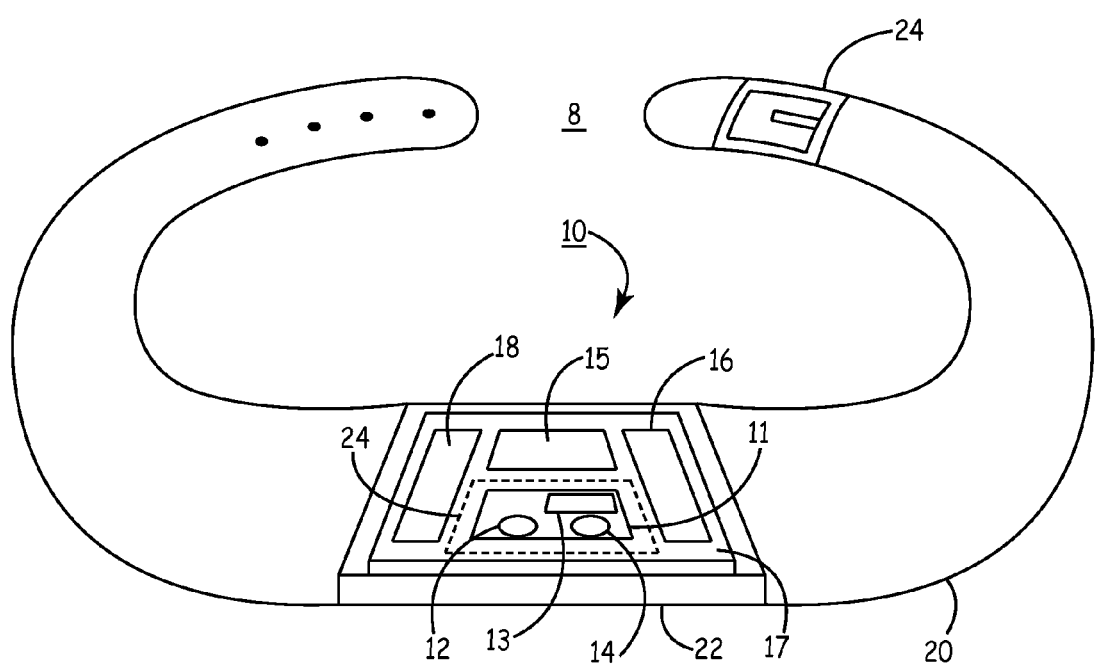
FIG. 1 is a conceptual diagram of a tissue perfusion monitor according to one embodiment.

FIG. 1 is a conceptual diagram of a tissue perfusion monitor 8 according to one embodiment. Tissue perfusion monitor 8 is configured as a wearable, external tissue perfusion monitor including a tissue perfusion sensor module 10 coupled to a wearable cuff 20. Wearable cuff 20 includes a fastener 24 for stably fastening cuff 20 around a part of the patient's body, such as a limb. For example, cuff 20 may be sized for wearing around a patient's wrist. Wearable cuff 20 is shown as a band with a buckle type fastener but may alternatively be provided in the form of a band with a Velcro, laced, snap, or other type of fastener to stably position cuff 20 around a portion of the patient's body, which may be around a leg, finger, abdomen, thorax, cranium, neck or other body part. Alternatively, cuff 20 may be formed from an elastic material for securely fitting cuff 20 around a body part without the use of a fastener 24.

Perfusion sensor module 10 includes a housing 22 enclosing circuitry for performing laser Doppler flowmetry (LDF). Housing 22 is coupled to cuff 20. Module 10 includes a LDF unit 11, a processor 15, and communication circuitry 16. A power source 18, which may be provided as a rechargeable or replaceable battery, provides power to the LDF unit 11, processor and control 15, communication circuitry 16 and any other components requiring power that may be included in module 10. In one embodiment, power source 18 is embodied as a rechargeable Li-ion battery pack providing power for the laser light source 12 and photodetector 14 included in LDF unit 11. It is recognized that in some embodiments, more than one battery may be provided for separately powering the LDF unit 11 and other module components (e.g., processor and control 15 and communication circuitry 16). When multiple batteries are included, any combination of rechargeable and replaceable batteries may be used.

Laser light source 12 is provided as a miniaturized coherent laser light source, such as a laser diode or vertical cavity surface emitting laser (VCSEL). To perform LDF, only a single light source is required. The laser light source is selected to provide a coherent beam of light centered on a wavelength in the visible to near infrared range, for example between approximately 600 and 1300 nm, though other wavelengths may be used successfully in obtaining a tissue perfusion measurement signal. The light source is provided with a narrow bandwidth of the emitted light wavelength, for example a spectral bandwidth of approximately 5 nm or less. In one embodiment, laser light source 12 is embodied is a VCSEL measuring approximately 300×300×150 $\mu m^3$, and emitting approximately 1 mW of light at a nominal wavelength of 785 nm and spectral width of approximately 0.8 nm. Processor 15 controls power supply 18 to deliver power to light source 12 when a tissue perfusion measurement is desired. The laser light source 12 is generally selected to have a low power consumption to reduce the battery size and/or increase longevity of the tissue perfusion monitor 10.

Photodetector 14 may be embodied as a photodiode, such as a PIN photodiode. In one embodiment, photodetector 14 is embodied as a PIN photodiode measuring approximately 100×100 $\mu m^2$ and having approximately 0.15 A/W sensitivity at 780 nm. Other components suitable for use as a light detector include a photoresistor, phototransistor, photovoltaic cell, photomultiplier tube, bolometer, charge-coupled device (CCD) or an LED reverse-biased to function as a photodiode.

Laser light source 12 and photodetector 14 may be integrated in a LDF hybrid circuit unit 11 that additionally includes photodetector conditioning circuitry 13, typically including an amplifier and filter. LDF unit 11 measures approximately 2×2 $cm^2$ in one embodiment and is mounted along a substrate 17, which may be a hybrid circuit board substrate carrying other sensor electronic components. Power source 18, processor and control 15, and communication circuitry 16 are additionally mounted along substrate 17 with appropriate electrical connection provided between the components of module 10 to achieve the functionality described herein.

Light emitted by laser light source 12 is scattered back to photodetector 14 causing an induced photodetector current signal. At least some of the back-scattered light is reflected off moving red blood cells producing a Doppler shifted component of the received light signal. An amplified and filtered photodetector signal is provided by conditioning circuitry 13 to processor 15. The photodetector signal is typically a current signal, but may be measured as a voltage signal in some embodiments.

Processor 15 controls emission of a light by laser light source 12 and receives a signal generated by photodetector 14 in response to the back-scattered light. Processor 15 computes a tissue perfusion measurement in response to the Doppler-shifted component of the photodetector current signal, which is correlated to the flow of blood in an adjacent tissue volume. A current signal generated by the photodetector may be processed in the time domain or in the frequency domain to obtain a measurement correlated to tissue perfusion. In one embodiment, processor 15 is configured to perform a spectral analysis on a defined frequency band-width of the photodetector signal to obtain a Doppler power spectrum.

The magnitude of the power spectrum is calculated to determine a perfusion signal as given by the following equation:

$$M_i = \int_a^b \omega^i P(\omega) d\omega$$

where Mi represents ith moment of the power spectra $P(\omega)$, $\omega$ represents each frequency content in the spectra and a and b are constants which define the spectral bandwidth.

The first moment of the power spectrum (M1) is correlated to the average concentration of moving red blood cells and the average root mean square (rms) velocity of the moving red blood cells in the measurement volume and can be referred to as "flux". The M1 signal, which is typically normalized by the photodetector DC output, is provided as a tissue perfusion signal in some embodiments. The M1 signal may used in an uncalibrated form and expressed in arbitrary perfusion units.

The zero moment, M0, of the power spectrum is equal to the modulation depth of the photodetector signal and is proportional to the concentration of moving red blood cells. In some embodiments M0 may be used to obtain a tissue perfusion signal. The first moment M1 normalized by the zero moment M0, i.e. M1/M0, is correlated to the speed of the moving blood cells and is an alternative signal that may be used in monitoring tissue perfusion. M1/M0 may be less desirable than M1 due to a non-linear response of M0 to red blood cell concentration under some conditions.

In some embodiments, the sensor module 10 may be calibrated to yield standardized measurements. The perfusion signal can be measured when the sensor module 10 is placed along a tissue phantom having a known concentration of a suspension. The tissue perfusion signal measured at one or more known concentrations may then be reported in standardized tissue perfusion units according to a known linear or non-linear response of the tissue perfusion signal to changes in perfusion. The tissue phantom may be designed to mimic pulsatile motion of blood with adjustable flow speeds. Sensor modules may be standardized in this way at the time of manufacture or prior to being positioned in or on a patient so that perfusion signal magnitudes are comparable between sensors and devices.

Communication circuitry 16 includes wireless transmission and receiving circuitry and an associated antenna for sending data to and receiving data from another device. Examples of medical device wireless communication systems that may be employed by the system of the present disclosure include, but are not limited to, the systems disclosed in commonly-assigned U.S. Pat. No. 7,013,178 (Reinke et al.) and U.S. Pat. No. 7,139,613 (Reinke et al.), the disclosures of which are incorporated herein by reference in relevant parts. Communication circuitry 16 is controlled by processor 15 to transmit perfusion signal data. Communication circuitry 16 may receive commands or requests for performing perfusion measurements from an external device or an implanted device, such as an ICD or pacemaker adapted for bidirectional communication with sensor module 10.

Figure 2:
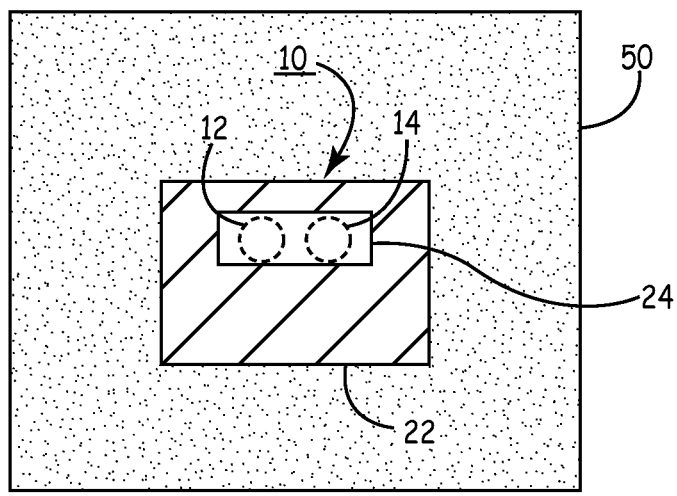
FIG. 2 is a bottom view of an alternative embodiment of a tissue perfusion monitor.

FIG. 2 is a bottom view of an alternative embodiment of a tissue perfusion sensor. Sensor module 10 is coupled to an adhesive patch 50 which may be worn by the patient on his or her skin. As described previously, sensor module 10 includes a housing 22 enclosing sensor circuitry, including laser light source 12 and photodetector 14 shown visible through a lens 24 positioned in an opening formed in housing 22 for passing emitted and back-scattered light. Lens 24 may be formed as a flat panel, cylinder or half-cylinder of glass, sapphire, ruby, quartz or any other suitable light transparent material. In some embodiments, a light barrier may be required between the light source 12 and the photodetector 14 to minimize light from the light source reaching the photodetector 14 directly.

Figure 3:
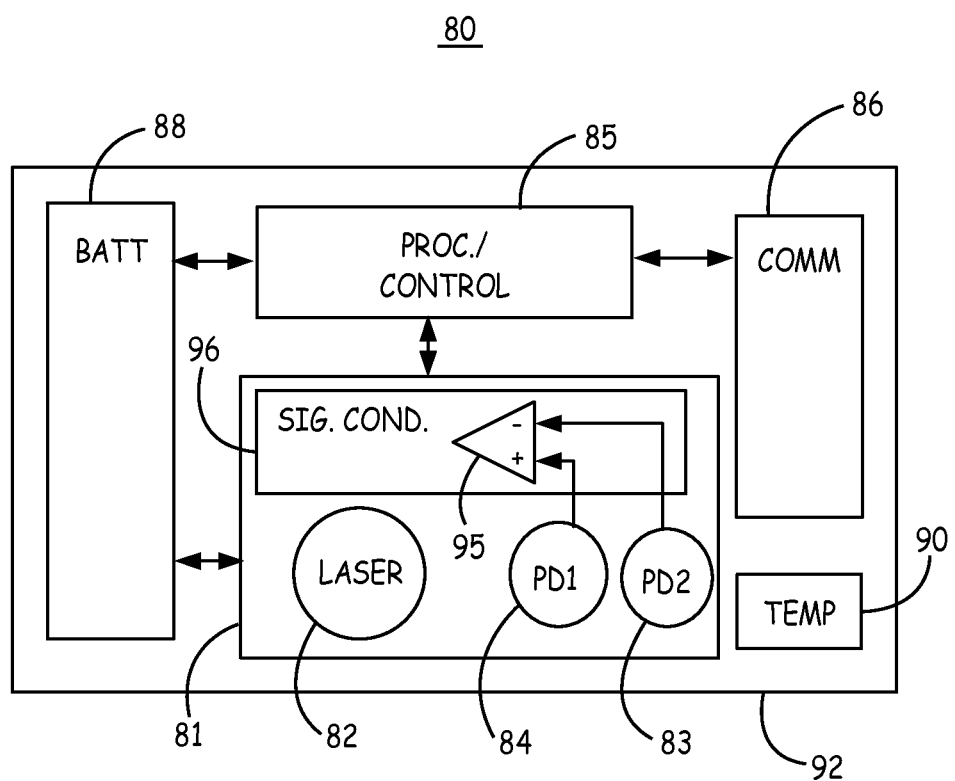
FIG. 3 is a functional block diagram of a tissue perfusion sensor module, according to one embodiment.

FIG. 3 is a functional block diagram of a tissue perfusion sensor module 80, according to an alternative embodiment. Module 80 includes a LDF unit 81 having a laser light source 82, a first photodetector 84, a second photodetector 83, and signal conditioning circuitry 96. The second photodetector 83 is positioned adjacent the first photodetector 84 to collect substantially the same light signal. Signal conditioning circuitry 96 is shown to include a differential amplifier 95. The differential amplifier 95 rejects common mode noise while still retaining the Doppler shifted light signal associated with moving blood cells in the adjacent tissue. Common mode noise may include laser light source noise 82 common to both photodetector channels (i.e. both photodetector signals).

Sensor module 80 further includes a battery 88 for powering the various sensor module components, such as laser light source 82, processor and control 85, communication circuitry 86 and a temperature sensor 90. Connections between some components shown in module 80 are shown and other connections are not shown for the sake of clarity. It is understood that components shown in module 80 are in electrical connection with each other, for example along a hybrid circuit board 92, as needed to perform the functionality described herein.

Processor and control 85 controls the emission of light by laser source 82 and receives a light signal from signal conditioning circuitry 96 for processing and computation of a tissue perfusion measurement. A tissue perfusion measurement signal or parameter values derived therefrom are provided to communication circuitry 86 for transmission to another device.

Temperature sensor 90 is included in module 80 for measuring temperature at the tissue perfusion measurement site. Since blood flow will vary with temperature, a temperature signal is provided to processor and control 85 for use in adjusting or correcting a tissue perfusion measurement signal for the effects of temperature changes. Temperature data may also be provided to communication circuitry 86 for transmission to another device with accompanying tissue perfusion data.

Figure 4:
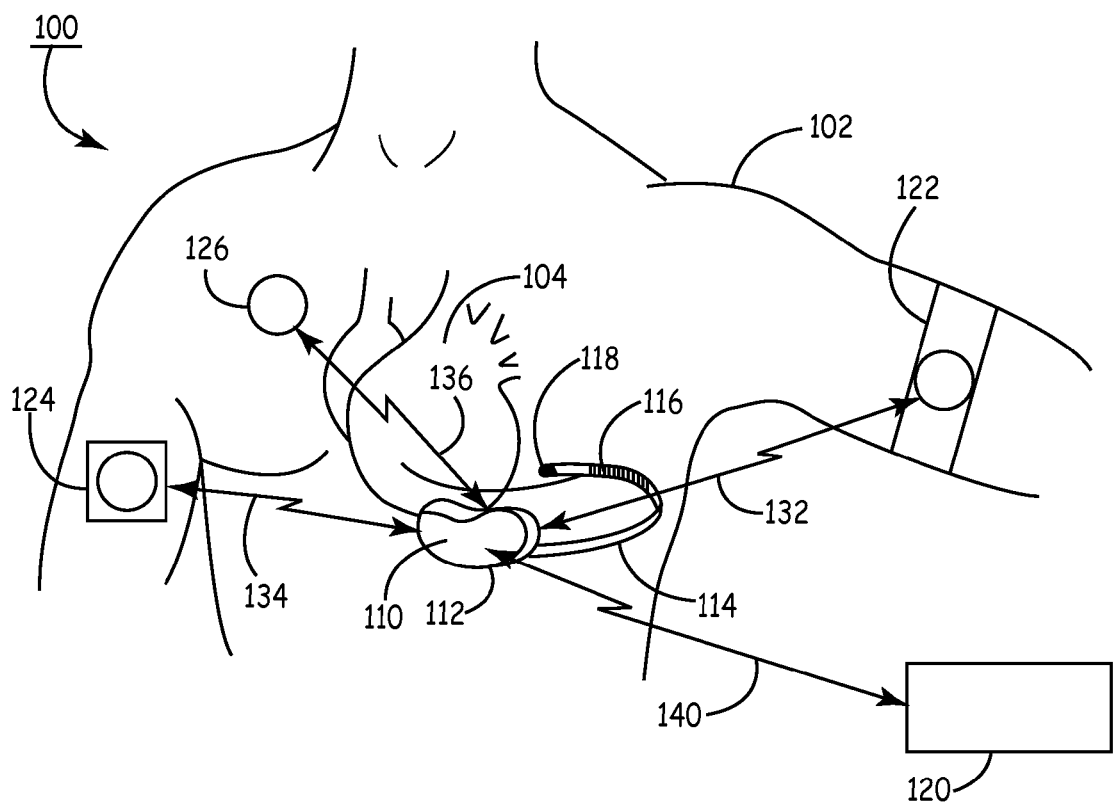
FIG. 4 is a schematic diagram of an implantable medical device system including a tissue perfusion sensor module.

FIG. 4 is a schematic diagram of an implantable medical device (IMD) system 100 including a tissue perfusion sensor module. As illustrated in FIG. 4, an IMD embodied as an ICD 110 is provided as a subcutaneous device in which both the ICD 110 and an associated lead 114 carrying a defibrillation coil electrode 116 are implanted outside the ribcage of the patient 102, subcutaneously or submuscularly. It is understood that while the subcutaneous ICD 110 may be positioned between the skin and muscle layer of the patient, the term "subcutaneous ICD" or generally a "subcutaneously" implantable device as referred to herein is intended to include a device and any associated leads that can be positioned in any extravascular location of the patient, such as below the muscle layer or within the thoracic cavity, for example.

Subcutaneous ICD 110 includes a housing 112 to enclose electronic circuitry of the device 110. Subcutaneous ICD 110 may correspond to a subcutaneous ICD as generally disclosed in U.S. Pat. No. 7,684,864 (Olson et al.) or U.S. Pat. No. 7,894,894 (Stadler, et al.), both of which patents are hereby incorporated herein by reference in their entirety.

A sensing and cardioversion/defibrillation therapy delivery lead 114 in electrical communication with subcutaneous ICD 110 is tunneled subcutaneously into a location adjacent to a portion of a latissimus dorsi muscle of patient 102. Specifically, lead 114 is tunneled subcutaneously from the median implant pocket of the subcutaneous device 112 laterally and posteriorly to the patient's back to a location opposite the heart 104 such that the heart 104 is disposed between the subcutaneous ICD 112 and the distal electrode coil 116 and distal sensing electrode 118 of lead 114 to enable cardioversion/defibrillation shock delivery and cardiac signal sensing. ICD 110 may incorporate sensing electrodes along the housing 112.

A programmer 120 is shown in telemetric communication with subcutaneous ICD 110 by a wireless communication link 140. A bidirectional communication link 140 may be established between ICD 110 and programmer 120 using any appropriate RF link such as Bluetooth, WiFi, or Medical Implant Communication Service (MICS). Programmer 120 is used to transmit operating commands, software, or data retrieval requests to IMD 110 and to receive data acquired by IMD 110.

The medical device system 100 includes at least one tissue perfusion monitor 122, 124 or 126. Monitors 122 and 124 are illustrated as external monitors worn by the patient as a wearable cuff monitor 122 or a wearable patch monitor 124. Monitor 126 is illustrated as an implantable tissue perfusion monitor that may be implanted at any desired body location for monitoring tissue perfusion. While FIG. 4 shows three tissue perfusion monitors 122, 124 and 126 to illustrate various monitor configurations and locations, it is recognized that only one monitor may be used with ICD 110 or multiple monitors may be used with ICD 110 for cooperatively detecting an unstable or deteriorating hemodynamic condition of patient 102.

Each of the monitors 122, 124 and 126 is shown having a bidirectional communication link 132, 134, and 136, respectively, with ICD 110, which may use any appropriate RF link such as Bluetooth, WiFi, or Medical Implant Communication Service (MICS) or other wireless communication technology for IMD systems. ICD 110 may request a tissue perfusion measurement from a monitor 122, 124, or 126. Tissue perfusion monitor 122, 124 or 126 responds by performing a measurement and transmitting a measurement signal back to ICD 110.

Subcutaneous ICD 110 is one illustrative embodiment of an implantable medical device that may operate cooperatively with a tissue perfusion monitor for monitoring a patient condition and/or controlling a therapy. The tissue perfusion monitor described herein may be implemented in conjunction with other types of implantable devices configured to detect a physiological condition and/or automatic therapy delivery, including ICDs coupled to transvenous leads, pacemakers, drug delivery pumps, hemodynamic monitors, ECG monitors, or the like.

In one embodiment, ICD 110 and lead 114 may be replaced by a dual chamber, biventricular or multi-chamber pacing device and associated transvenous leads. For example, IMD system 100 may alternatively include one or more of tissue perfusion monitors 122, 124, 126 positioned at desire monitoring site(s) and a cardiac pacemaker and associated leads for delivering CRT. A pacemaker and associated leads for delivering CRT is generally disclosed in U.S. Pat. No. 7,092,759 (Nehls, et al.), hereby incorporated herein by reference in its entirety.

Figure 5:
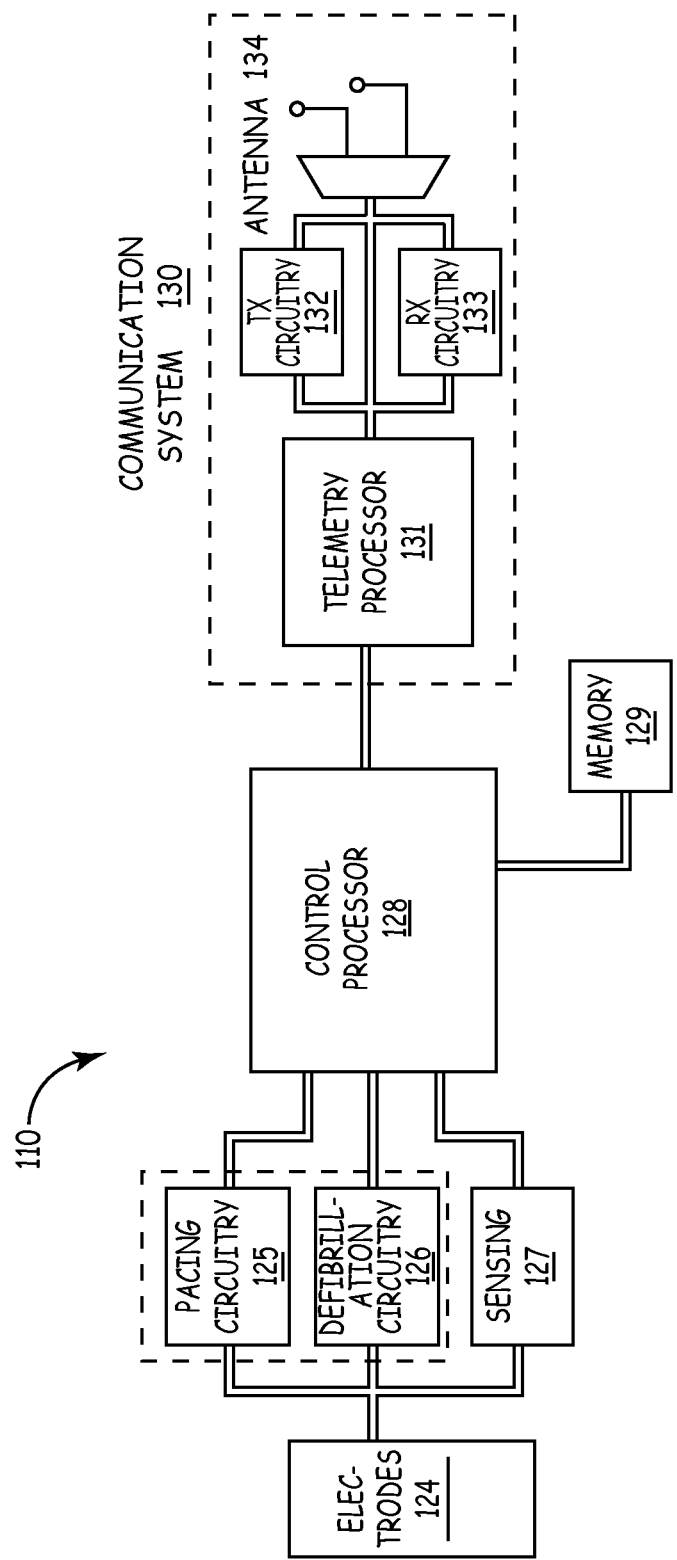
FIG. 5 is a functional block diagram of ICD.

FIG. 5 is a functional block diagram of ICD 110. Circuitry located within ICD 110 of FIG. 4 includes defibrillation circuitry 126, sensing circuitry 127, and may include pacing circuitry 125. In alternative embodiments, an IMD used in conjunction with a tissue perfusion monitor may include pacing circuitry 125 without defibrillation capabilities. Electrodes 124 carried by leads coupled to ICD 110 and/or incorporated along the ICD housing are connected to pacing circuitry 125, defibrillation circuitry 126 and sensing circuitry 127. Each lead (and in turn individual electrodes associated with each lead) coupled to the ICD may be used in multiple capacities to sense cardiac depolarizations (e.g. P-waves and R-waves), deliver pacing pulses including anti-tachycardia pacing (ATP) pulses, and deliver defibrillation or cardioversion shocks.

Control processor 128 receives input through sensing circuitry 127 from electrodes 124 concerning cardiac depolarizations sensed by the electrodes connected to sensing circuitry 127. Based on input received from sensing circuitry 127, control processor 128 performs an arrhythmia detection algorithm for detecting arrhythmias and selecting a therapy as needed. Therapy may include providing ATP therapy using pacing circuitry 125 and selected pacing electrodes, providing defibrillation or cardioversion shocks using defibrillation circuitry 126 and a selected high voltage electrode, or providing no treatment at all.

Control processor 128 stores selected data to memory 129, and retrieves stored data from memory 129 as necessary. Communication system 130 includes telemetry processor 131, transmission circuitry 132, receiving circuitry 133, and antenna 134. Communication system 130 allows communication between ICD 110 and devices external to the patient as well as a tissue perfusion monitor as described above. ICD 110 is configured to perform bi-directional telemetric communication with a tissue perfusion monitor for requesting and receiving a tissue perfusion signal. Control processor 128 uses the tissue perfusion signal in detecting an arrhythmia or verifying an arrhythmia detection made based on a cardiac electrical signal. Control processor selects a therapy based at least in part on the tissue perfusion signal. Circuitry included in ICD 110 for controlling the delivery of arrhythmia therapies may correspond to ICD circuitry generally described in commonly-assigned U.S. Pat. No. 6,259,947 (Olson et al.), hereby incorporated herein by reference in its entirety.

Figure 6:
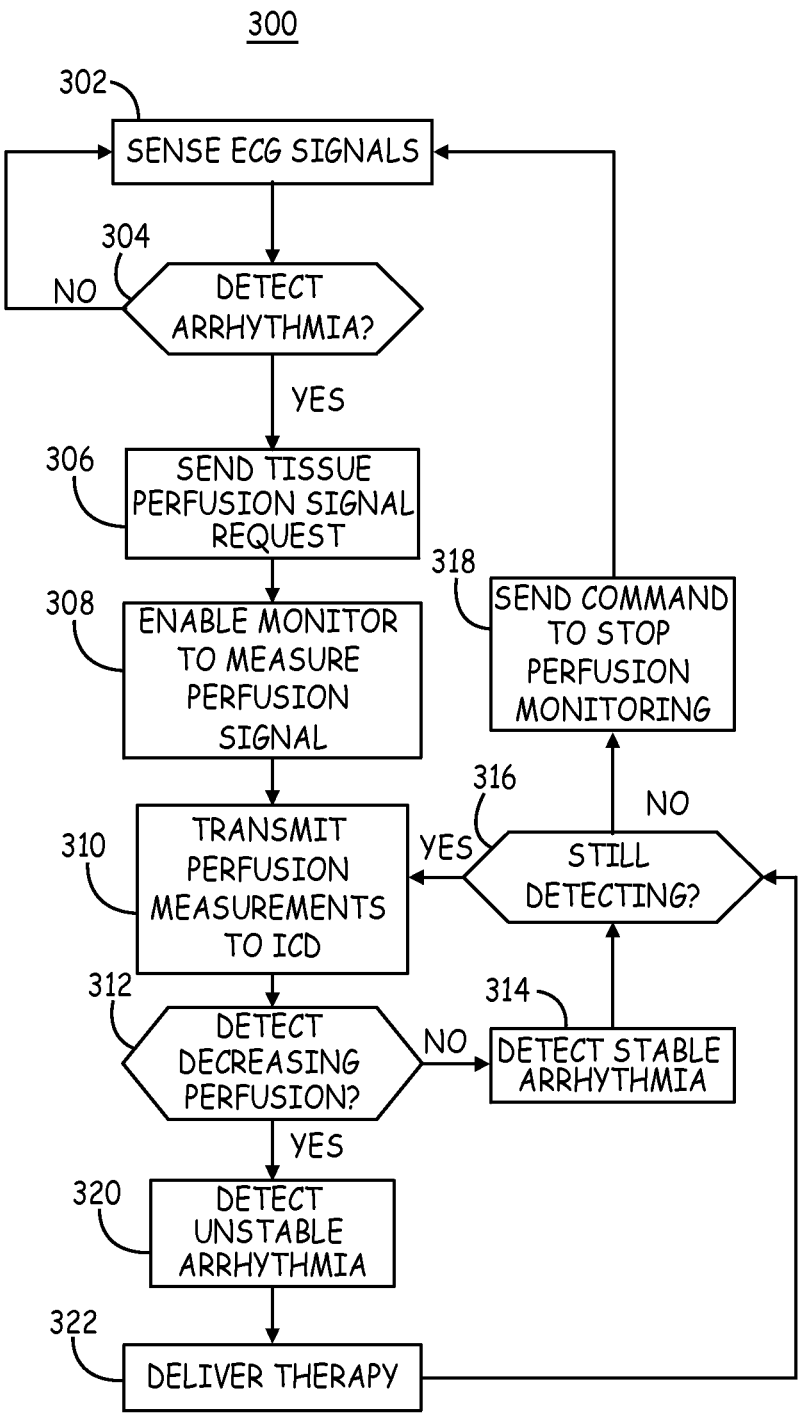
FIG. 6 is a flow chart of a method for monitoring tissue perfusion for use in detecting hemodynamically unstable arrhythmias.

FIG. 6 is a flow chart 300 of a method for monitoring tissue perfusion for use in detecting hemodynamically unstable arrhythmias. Flow chart 300 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern implantable medical device system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The method shown by flow chart 300 is performed by a medical device system including an ICD and an implanted or externally worn tissue perfusion monitor, such as the system shown in FIG. 4. At block 302, the ICD senses ECG signals (or EMG signals if intracardiac electrodes are coupled to the ICD) for use in detecting an arrhythmia at block 304 according to detection algorithms implemented in the ICD. An arrhythmia detection algorithm is typically implemented for detecting ventricular tachycardia (VT) or ventricular fibrillation (VF) but other arrhythmias such as supraventricular tachycardia (SVT) may also be detected or discriminated.

When a VT or VF is detected that is potentially hemodynamically unstable requiring a cardioversion/defibrillation shock, the ICD transmits a request for a tissue perfusion signal to the tissue perfusion monitor at block 306. At block 308, the tissue perfusion monitor enables the laser light source to emit light and the monitor processor receives the photodetector signal for determining tissue perfusion measurements. A tissue perfusion measurement may be measured at regular intervals of time, e.g. once per second, every two seconds, every five seconds or other interval to determine if the detected arrhythmia is associated with a decreasing trend in tissue perfusion.

At block 310, the tissue perfusion measurements are wirelessly transmitted to the ICD. The ICD compares the tissue perfusion measurements to detect a decreasing trend in perfusion at block 312. Tissue perfusion measurements may be sampled several times a second, once per second or less, but will typically be monitored over a short interval of time, for example 10 seconds or less, to enable quick detection of an unstable rhythm requiring shock delivery. If decreasing perfusion is not detected, the arrhythmia is determined to be a hemodynamically stable arrhythmia at block 314. The ICD will withhold ventricular cardioversion/defibrillation therapy. In some embodiments, other therapies, such as anti-tachycardia pacing may be delivered.

If the ICD is still detecting an arrhythmia based on cardiac electrical activity, as determined at decision block 316, the tissue perfusion monitor continues to measure a perfusion signal and transmit the signal to the ICD. A sustained arrhythmia may deteriorate from a hemodynamically stable rhythm to a hemodynamically unstable rhythm. If the ICD is no longer detecting an arrhythmia (decision block 316), the ICD sends a command to the tissue perfusion monitor at block 318 to stop measuring tissue perfusion and stop transmission of the tissue perfusion signal. The process returns to block 302 where the ICD continues to sense the ECG (or EGM) signal for detecting arrhythmias.

If decreasing tissue perfusion is detected at block 312 by the ICD in response to the tissue perfusion signal received from the tissue perfusion monitor, the arrhythmia is detected as an unstable arrhythmia at block 320. The ICD delivers a cardioversion/defibrillation therapy at block 322 to promptly terminate the unstable arrhythmia according to programmed therapy delivery parameters. After delivering the therapy at block 322, if the ICD is still detecting an arrhythmia at decision block 316, the tissue perfusion signal continues to be measured and transmitted to the ICD at block 310. It is understood that multiple shocks may be delivered in some cases in order to terminate the arrhythmia.

If the arrhythmia is no longer detected at block 316, the tissue perfusion monitoring and transmission of the tissue perfusion signal is stopped at block 318 by a command sent from the ICD to the tissue perfusion monitor. The process returns to block 302.

Figure 7:
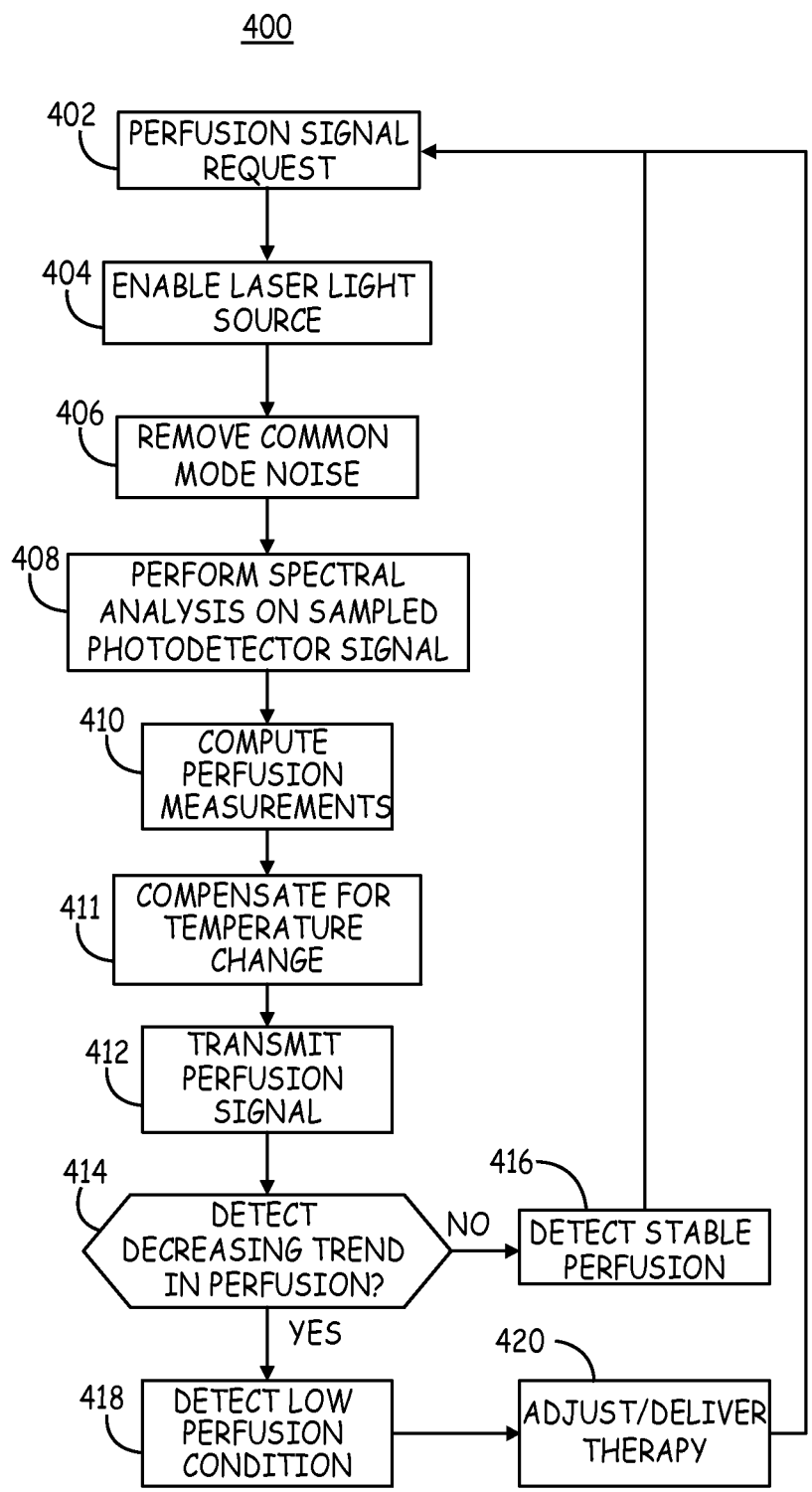
FIG. 7 is a flow chart of one method for measuring a tissue perfusion signal.

FIG. 7 is a flow chart 400 of one method for measuring a tissue perfusion signal. At block 402, the tissue perfusion monitor receives a wireless signal from another medical device indicating a request for a tissue perfusion signal. The monitor enables the laser light source to emit light at block 404. At block 406, an induced photodetector current signal undergoes filtering, amplification, and a second photodetector signal may be used to remove common mode noise from the photodetector signal as described previously.

At block 408, the photodetector signal is processed to provide a tissue perfusion measurement, e.g. a normalized measurement of M1 as described previously, at block 410. The photodetector signal may be sampled at a relatively high rate, for example a sampling rate between approximately 1 and 15 kHz may be used. In some embodiments, sampling may be less than 1 kHz or more than 15 kHz. The sampling rate selected will depend at least in part on the processing power and available power supply of the monitor. The spectral analysis performed at block 408 is performed on the sampled signal to obtain a tissue perfusion measurement at rates of several times per second, once per second or less often as required by a monitoring algorithm. For example, perfusion measurements may be sampled every second for a desired interval of time allowing the perfusion measurements to be compared to each other for detecting an increasing, decreasing or stable trend in tissue perfusion.

Alternatively, measurements of perfusion may be sampled over a defined interval of time and averaged together to obtain an average perfusion measurement. An averaged measurement can be compared to an average perfusion measurement obtained for an earlier time period. Average tissue perfusion measurements may be obtained according to a periodic tissue perfusion monitoring algorithm or in response to a trigger based on another physiological signal or a change in a delivered therapy. For example, perfusion measurements may be determined once per second for five to ten seconds or more then averaged to obtain an average tissue perfusion measurement at a given time point. Averaged perfusion measurements obtained once per hour, every four hours, every eight hours, once per day, once per week, or other scheduled time interval may be compared to determine trends in tissue perfusion over relatively longer periods of time. It is recognized that the time intervals for determining a tissue perfusion measurement and time intervals between measurements being compared will vary depending upon the particular monitoring application.

The tissue perfusion signal, which may be a measurement of M1 as described above or other parameter determined from the Doppler-shifted light signal, may be compensated or corrected for temperature changes at block 411. A signal received from a temperature sensor and correlated to changes in temperature at the monitoring site is used by the monitor processor to adjust the tissue perfusion measurements according to temperature changes. A temperature correction factor may be determined prospectively during a sensor calibration procedure in which the temperature sensor response and the tissue perfusion sensor response to known changes in actual temperature are recorded. Alternatively, temperature data is stored along with tissue perfusion measurements to allow changes in perfusion to be interpreted in light of temperature changes.

The temperature-compensated tissue perfusion signal is transmitted from the tissue perfusion monitor to the requesting device at block 412. The requesting device compares perfusion measurements sampled over time at block 414. If the tissue perfusion signal is decreasing, low perfusion is detected at block 418. If not, stable perfusion is detected at block 416. Alternatively the perfusion measurement comparison may be performed by a comparator included in the tissue perfusion monitor and a signal indicating decreasing perfusion, increasing perfusion, or stable perfusion is transmitted to the requesting device.

In response to detecting a low perfusion condition, i.e. a decreasing perfusion trend, a therapy is adjusted or delivered at block 420. In the case of the requesting device being an ICD, a cardioversion/defibrillation shock may be delivered at block 420 based on the verification of a hemodynamically unstable arrhythmia as evidenced by a decreasing tissue perfusion signal. In other embodiments, a comparative analysis of tissue perfusion measurement obtained during a cardiac pacing optimization procedure may be performed to identify pacing or CRT parameters that yield the highest or optimal tissue perfusion. The pacing or CRT pacing parameters are adjusted to the optimal settings at block 420.

The perfusion measurement may be used as a surrogate for cardiac output or blood pressure measurements in any therapy management application. A therapy may be optimized or adjusted to maintain an optimal hemodynamic status of the patient. A method for optimizing CRT which may be adapted to implement a tissue perfusion measurement as described herein is generally described in U.S. Pat. No. 7,769,451 (Yang, et al.), hereby incorporated herein by reference in its entirety.

As such, the tissue perfusion monitor described herein may be implemented in systems used for treating patients for cardiac arrhythmias, heart failure, or hypertension among other conditions. Furthermore, a tissue perfusion monitor as described herein may be implemented in systems that do not include therapy delivery capabilities. The tissue perfusion measurements may be monitored and recorded over time for detecting heart failure decompensation or other hemodynamic events that manifest in decreased tissue perfusion.

Thus, a tissue perfusion monitor and associated methods have been presented in the foregoing description with reference to specific embodiments. It is appreciated that various modifications to the referenced embodiments may be made without departing from the scope of the disclosure as set forth in the following claims.

The invention claimed is:

1. A system for monitoring tissue perfusion in a patient, comprising:
   an implantable medical device comprising:
      a plurality of electrodes for sensing a cardiac signal,
      a sensing circuit coupled to the plurality of electrodes,
      a communication system configured to perform bi-directional wireless telemetry communication, and
      a control processor configured to:
         receive the sensed cardiac signal through the sensing circuitry,
         detect an arrhythmia in response to the sensed cardiac signal,
         responsive to detecting the arrhythmia, transmit a request for a tissue perfusion measurement via the communication system; and
   a tissue perfusion monitor comprising:
      a laser Doppler unit comprising a coherent laser light source and a first photodetector;
      a processor configured to receive a signal from the photodetector and directly determine a blood flow measurement of a tissue volume adjacent to the photodetector responsive to a Doppler-shifted component of the photodetector signal, wherein the tissue perfusion measurement corresponds to the blood flow measurement;
      a wireless communication circuit configured to receive the request for the tissue perfusion measurement, determine the blood flow measurement, and transmit the blood flow measurement to the implantable medical device;
      a power source providing power to the laser Doppler unit, the processor and the communication circuit; and
      a housing enclosing the laser Doppler unit, the processor, the power source and the communication circuit.

2. The system of claim 1 further comprising means for securing the housing to the patient to position the laser Doppler unit adjacent the patient's skin.

3. The system of claim 1 wherein the power source comprises a rechargeable battery.

4. The system of claim 1 wherein the laser light source comprises a vertical cavity surface emitting laser.

5. The system of claim 1, wherein the implantable medical device further comprises a therapy circuit coupled to the electrodes for delivering a therapy to treat the arrhythmia, the processor controlling the therapy circuit to withhold the therapy in response to the tissue perfusion measurement.

6. The system of claim 5, wherein the implantable medical device therapy circuit comprises a pulse generator for generating a shock pulse, wherein the processor controls delivery of the shock pulse by the therapy circuit in response to the tissue perfusion measurement.

7. The system of claim 6 wherein the processor is configured to control the therapy circuit to deliver the shock pulse in response to the tissue perfusion measurement corresponding to a decreasing tissue perfusion trend.

8. The system of claim 5, wherein the implantable medical device therapy circuit comprises a pacing circuit for delivering cardiac pacing pulses, the processor configured to control a cardiac pacing pulse delivery parameter of the pacing circuit in response to the tissue perfusion measurement.

9. The system of claim 1 further comprising a temperature sensor for sensing a body temperature,
   the processor configured to adjust the tissue perfusion measurement using the body temperature measurement.

10. The system of claim 1 further comprising a second photodetector,
    the laser Doppler unit comprising a differential amplifier for removing common mode noise from the first photodetector signal using a signal from the second photodetector.

11. A method for monitoring tissue perfusion in a patient, comprising:
    receiving a cardiac signal by a control processor of an implantable medical device through sensing circuitry coupled to a plurality of electrodes;
    detecting an arrhythmia by the control processor in response to the received cardiac signal;
    responsive to detecting the arrhythmia, transmitting a request for a tissue perfusion measurement via a communication system of the implantable medical device;

receiving the request for the tissue perfusion measurement by a wireless communication circuit of a tissue perfusion monitor that comprises:
- a coherent laser light source a first photodetector, a processor, a power source and a communication circuit all enclosed within a housing;
- activating the coherent laser light source to emit light in response to the request for the tissue perfusion measurement;
- measuring a Doppler-shifted component of a photodetector signal in response to the emitted light;
- determining a blood flow measurement of a tissue volume adjacent to the photodetector responsive to the Doppler-shifted component of the photodetector signal, wherein the tissue perfusion measurement corresponds to the blood flow measurement; and
- wirelessly transmitting the blood measurement to the implantable medical device communication system.

12. The method of claim 11 wherein activating the laser light source comprises activating a vertical cavity surface emitting laser.

13. The method of claim 11 further comprising:
- receiving by the implantable medical device communication system the transmitted tissue perfusion measurement, and
- controlling a therapy delivery circuit of the implantable medical device to withhold an anti-arrhythmia therapy in response to the tissue perfusion measurement.

14. The method of claim 13, further comprising controlling delivery of a shock pulse by the implantable medical device therapy delivery circuit in response to the tissue perfusion measurement.

15. The method of claim 14, further comprising delivering the shock pulse in response to the tissue perfusion measurement corresponding to a decreasing tissue perfusion trend.

16. The method of claim 13, further comprising controlling the therapy delivery circuit to adjust a cardiac pacing pulse delivery parameter in response to the tissue perfusion measurement and delivering cardiac pacing pulses by the therapy delivery circuit according to the cardiac pacing pulse delivery parameter.

17. The method of claim 11, further comprising;
- measuring a body temperature by a temperature sensor of the tissue perfusion monitor; and
- adjusting the tissue perfusion measurement using the body temperature measurement.

18. The method of claim 11, further comprising:
- sensing a second photodetector signal from a second photodetector enclosed in the housing of the tissue perfusion monitor; and
- removing common mode noise from the first photodetector signal using the signal from the second photodetector.

19. A non-transitory computer readable medium storing instructions that cause a tissue perfusion monitoring system to:
- detect an arrhythmia by a control processor of an implantable medical device configured to sense cardiac signals from a plurality of electrodes;
- responsive to detecting the arrhythmia, transmit a request for a tissue perfusion measurement via a communication system of the implantable medical device;
- receive the request for the tissue perfusion measurement by a wireless communication circuit of a tissue perfusion monitor that comprises a coherent laser light source and a photodetector, a processor, a power source and a communication circuit within a housing,
- activate the coherent laser light source to emit light in response to the request for the tissue perfusion measurement;
- measure a Doppler-shifted component of a signal from the photodetector in response to the emitted light;
- determine a blood flow measurement of a tissue volume adjacent to the photodetector responsive to a Doppler-shifted component of the photodetector signal, wherein the tissue perfusion measurement corresponds to the blood flow measurement; and
- wirelessly transmit the tissue perfusion measurement to the implantable medical device communication system.

\* \* \* \* \*